United States Patent
Field et al.

(10) Patent No.: US 7,321,047 B2
(45) Date of Patent: Jan. 22, 2008

(54) SEPARATION OF TETRAHYDROCANNABINOLS

(75) Inventors: Jason Edward Field, Mississauga (CA); Jan Oudenes, Aurora (CA); Boris Ivanovich Gorin, Oakville (CA); Ricardo Orprecio, Etobicoke (CA); Fabio Eduardo Silva e Souza, Mississauga (CA); Navindra Jainarine Ramjit, Hamilton (CA); Emma-Louise Moore, Mississauga (CA)

(73) Assignee: Alphora Research Inc., Mississauga, Ontario (CA)

( * ) Notice: Subject to any disclaimer, the term of this patent is extended or adjusted under 35 U.S.C. 154(b) by 282 days.

(21) Appl. No.: 11/132,251

(22) Filed: May 19, 2005

(65) Prior Publication Data

US 2006/0264647 A1    Nov. 23, 2006

(51) Int. Cl.
*C07D 311/80* (2006.01)
(52) U.S. Cl. .................................................. 549/390
(58) Field of Classification Search ................ 549/390
See application file for complete search history.

(56) References Cited

U.S. PATENT DOCUMENTS 3,636,058 A * 1/1972 Fahrenholtz ................ 549/280

OTHER PUBLICATIONS

Gaoni et al, JACS, 93(1), p. 217-224 (1971).*
Powell G et al., "Science", vol. 93 No. 2422 pp. 522-523 (1941).

Gaoni Y. and Mechoulan R., J.A.C.S. "Communications to the Editor", vol. 86, pp. 1646-1647, (1964).

* cited by examiner

*Primary Examiner*—Bernard Dentz
(74) *Attorney, Agent, or Firm*—Robert G. Hirons

(57) ABSTRACT

An individual tetrahydrocannabinol isomer of interest is separated from a mixture containing two or more such isomers, by treating the mixture with an isocyanate or isothiocyanate of formula I:

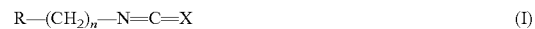

where R represents an aromatic ring optionally substituted with one or more electron withdrawing groups, n=0 or 1 and X is oxygen or sulphur; so as to produce a crystallizable THC carbamate of formula II:

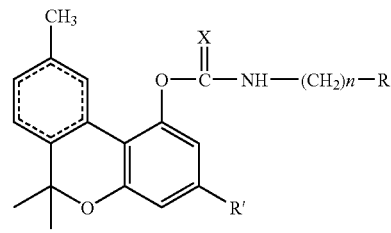

wherein X and R are as defined above, R' is a $C_3$-$C_{10}$ alkyl group and the dotted lines indicate optional unsaturation including aromatic, separating the compound of formula II from solution in isolation of other THC derivatives, and hydrolyzing the compound of formula II to form the individual tetrahydrocannabinol isomer of interest.

12 Claims, No Drawings

SEPARATION OF TETRAHYDROCANNABINOLS

FIELD OF THE INVENTION

This invention relates to tetrahydrocannabinols, and processes for their preparation. More particularly, it relates to processes for separation of individual tetrahydrocannabinols from mixtures of related compounds including different isomers of them.

BACKGROUND OF THE INVENTION

Tetrahydrocannabinols are the active constituents of marihuana (hashish). They can be represented by the general chemical formula:

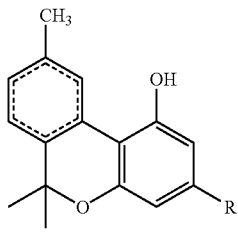

where R represents an alkyl chain of 3-10 carbon atoms, most commonly C5, and the dotted line represents optional unsaturation, including aromatic rings. The $\Delta^1$-3,4-trans-isomer, also referred to as $\Delta^9$-THC or dronabinol and having the chemical formula:

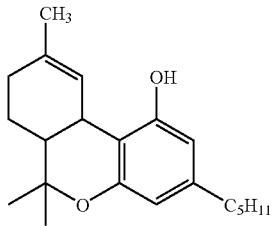

is the only active major constituent in hashish. It is physiologically active, and finds pharmaceutical use as an anti-emetic, e.g. for enhancing the appetite in patients suffering the side effects of chemotherapy, suffering from AIDS or anorexia. Other active homologs which have been reported are $\Delta^8$-THC, of formula:

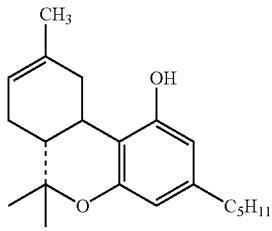

reported to be present in marihuana at about one-tenth of the amount of $\Delta^9$-THC, and a compound of the formula of $\Delta^9$-THC but in which the pentyl substituent group is replaced by a propyl group, and identified in Pakistani hashish.

Active tetrahydrocannabinols are found in only very small quantities in the natural plant extracts. Moreover, they are found in admixture with a significant number of chemical isomers, from which it is very difficult to separate and purify the active compound(s). This is so also with synthetic THCs—synthetic processes for the most part produce mixtures of isomers. The separation and purification process is complicated by the fact that THCs are oils by nature, largely on account of the presence in the molecular structure of the alkyl group.

BRIEF REFERENCE TO THE PRIOR ART

Powell G et.al., "Science", Vol. 93 No. 2422 Pages 522-523 (1941) disclose a crystalline 3,5-dinitrophenyl urethane derivative of tetrahydrocannabinol, hydrolysable to an active product. This compound was identified as a minor product in the mixture obtained from the red oil distillates of marihuana, by subjecting the oil distillates to distribution between petroleum ether and methanol, repeated extraction with alkali and distillation of the residues followed by chromatographic adsorption on alumina.

Gaoni Y. and Mechoulan R., J.A.C.S. "Communications to the Editor", Vol. 86, pp. 1646-7, 1964, and, in more detail, at J.A.C.S., 93:1 Jan. 13, 1971, pp 217-224 describe the purification of natural $\Delta^9$-THC via the crystalline 3,5-dinitrophenylurethane derivative, of formula:

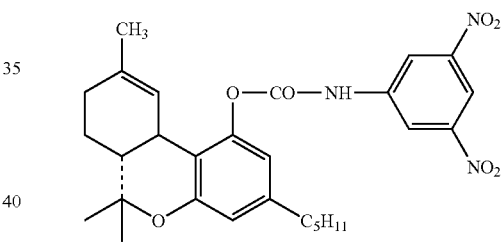

This compound was reportedly prepared by boiling $\Delta^9$-THC with 3,5-dinitrobenzoyl azide. The compound was dissolved in benzene, chromatographed on silica gel, eluted out with ether in pentane, and recrystallized from pentane. It was then hydrolyzed to form $\Delta^9$-THC using hydroalcoholic potassium hydroxide solution, and the $\Delta^9$-THC purified by chromatography. The authors report that this process yields a product which does not differ by any of the standard criteria of purity from the product as obtained after repeated chromatography. Moreover, this is not a procedure or intermediate product for use on a commercial scale, largely because of the potentially hazardous requirement for boiling with dinitrobenzoyl azide, a potentially explosive product and process.

It is an object of the present invention to provide novel processes and intermediates for the isolation and purification of THCs such as dronabinol which reduce one or more of the disadvantages with prior art processes.

It is a further object of the present invention to provide processes and intermediates for the isolation and purification of THCs such as dronabinol, which can substantially increase the efficiency of separation processes, and in this and other respects are suitable for operation on a commercial scale.

SUMMARY OF THE INVENTION

It has now been found that crystalline compounds can be prepared from THCs by reacting them with isocyanates or isothiocyanates. Reaction takes place at the phenolic group, to produce crystalline compounds capable of fractional crystallization to provide substantially pure, individual THC isomeric compounds, which can then be readily hydrolyzed to the THC isomer itself. In this way, different individual isomers including stereoisomers of THCs, such as dronabinol, can be obtained in essentially pure form, and by a process capable of being operated on a commercial scale. The invention also provides novel, crystallizable derivatives of THCs.

Thus according to one aspect of the present invention there is provided a process of separating an individual tetrahydrocannabinol isomer of interest from a mixture containing two or more such isomers, which comprises:

treating the mixture with an aromatic isocyanate or aromatic isothiocyanate of formula I:

R—(CH$_2$)$_n$—N═C═X            (I)

where R represents an aromatic ring optionally substituted with one or more electron withdrawing groups, X is oxygen or sulphur, and n is 0 or 1; so as to produce a crystallizable THC compound of formula II:

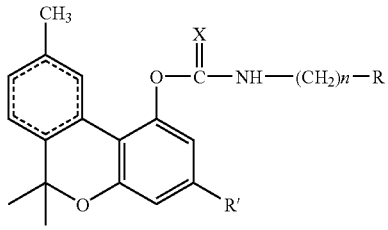

wherein X, n and R are as defined above, R' is a C$_3$-C$_{10}$ alkyl group and the dotted lines indicate optional unsaturation including aromatic;

forming a solution of the compound of formula II so formed in an organic solvent;

separating the compound of formula II from the solution in isolation of other THC derivatives;

and hydrolyzing the compound of formula II to form the individual tetrahydrocannabinol isomer of interest.

From another aspect, the invention provides novel, crystallizable tetrahydrocannabinol carbamate derivatives of the general formula:

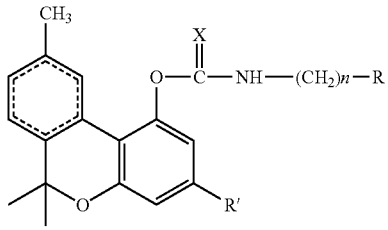

wherein R' is a C$_3$-C$_{10}$ alkyl group;

X is oxygen or sulphur;

n is 0 or 1 and R represents an aromatic ring optionally substituted with one or more electron withdrawing groups, with proviso that R is not 3,5-dinitrophenyl;

and the dotted lines indicate optional unsaturation including aromatic.

DESCRIPTION OF THE PREFERRED EMBODIMENTS

The aromatic group of the isocyanate or isothiocyanate reagent and intermediate product can be a phenyl group or a naphthyl group, optionally carrying one or more nuclear substituents independently selected from halo, cyano, sulfonate, carboxylate, carboxylic acid, aldehyde, keto, nitro, tertiary amino, trichloromethyl and trifluoromethyl. When benzyl is chosen, i.e. n=1 of formula:

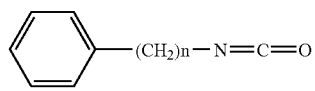

or benzyl isothiocyanate, with the result that the benzene ring is linked to the carbamate group through the intermediary of a methylene group, electron-withdrawing substituents on the benzene nucleus are not necessary. When the benzene or naphthalene ring links directly to the carbamate group, i.e n=0, one or more electron withdrawing groups should be present for best results. The crystallizability of the carbamate compound, on which the operation of the process of the invention depends, is believed to derive from the hydrogen bonding of the C═O or C═S and N—H groups of the carbamate structure, and the interaction of the n electrons of the aromatic terminal group therewith, an interaction which is increased by the electron-withdrawing nature of the chosen aromatic group.

Largely on grounds of cost and efficiency, benzyl isocyanate is most preferred, i.e. X being O, R being phenyl and n=1 in the above general formulae. This compound is particularly easily hydrolyzed to the THC.

When dronabinol is the THC of interest in the process, as is most preferred, of formula:

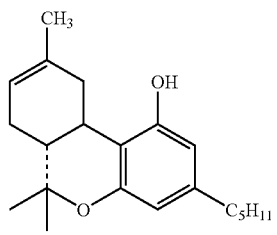

it reacts with the isocyanate to form a crystallizable compound, preferably:

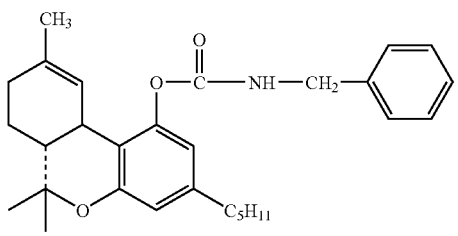

Other THC isomers in the mixture may similarly react to form carbamate compounds, depending on the constituents of the mixture being treated. If they do, the physical properties of them are sufficiently different from those of the dronabinol carbamate compound to allow its ready separation and isolation. Others will not react with the isocyanate, but will remain as an oily product, readily separated from the crystallized dronabinol carbamate compound.

The preferred process of the present invention is capable of producing dronabinol of a degree of purity unobtainable by chromatographic separation processes in any significant yield. In excess of 98.5% purity is obtainable, with a level of individual impurities below a range of purity important to achieve in respect of potential pharmaceutical compounds. Moreover, the preferred process avoids the need for extensive chromatographic separation steps, which are generally not economically viable on a commercial scale.

The intermediate carbamate compounds of the preferred embodiments of the invention are storage stable, and can be transported safely and without significant risk of degradation. This gives the manufacturer additional flexibility in the manufacturing process, with regard to timing and location and the like. In contrast, the final product dronabinol is sensitive to light and oxygen, so that it is not storage stable unless careful and expensive storage conditions are arranged for it. The process of the invention thus affords to the manufacturer the possibility of stable storage of the intermediate, and conversion thereof to unstable dronabinol as required, to minimize storage of dronabinol with attendant risk of product losses.

The invention is further described, for illustrative purposes, in the following specific example.

SPECIFIC DESCRIPTION OF THE MOST PREFERRED EMBODIMENT

Synthetic Scheme:

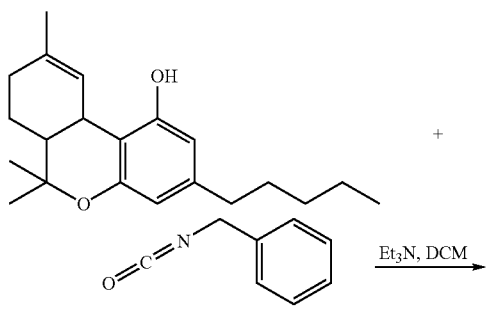

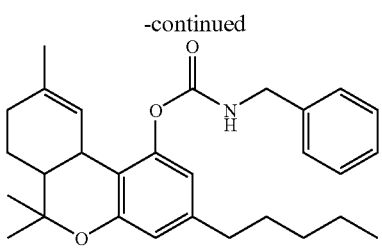

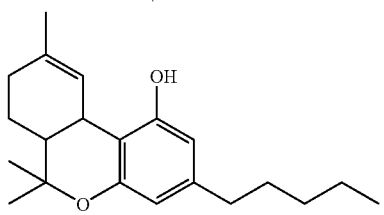

A 100 mL round-bottom flask equipped with a magnetic stir bar and nitrogen inlet was charged with dronabinol (2.0 g, 6.36 mmol) (96.9% a/a purity by HPLC, obtained after repeated chromatography steps) and 40 mL of dichloromethane. Benzyl isocyanate (0.93 g, 6.98 mmol) was slowly added to the reaction mixture with agitation. Triethylamine (0.160 mL, 1.15 mmol) was added and the reaction mixture agitated for 3 h at ambient temperature after which time the reaction was deemed complete as indicated by TLC (4:1 hexane:EtOAc). The reaction mixture was concentrated by rotary evaporation and the crude residue was purified by column chromatography (using 9:1 hexane:EtOAc as the eluent) to give 1.61 g (57% yield) of the benzyl carbamate derivative (94.3% a/a HPLC purity).

1.2 g of the benzyl carbamate derivative was combined with 5 mL of hexane and heated gently until completely dissolved. The solution was cooled to ambient temperature and the resulting crystals were collected by vacuum filtration. A second crop was also obtained by cooling the filtrate. The combined crops gave 0.83 g (69% recovery) of the benzyl carbamate derivative (98.8% a/a purity by HPLC).

A sample of the purified benzyl carbamate derivative (0.20 g, 0.447 mmol) was combined with $K_2CO_3$ (0.33 g, 2.4 mmol), 3 mL of water and ethanol (added until a homogeneous solution was obtained). The reaction mixture was stirred at ambient temperature for ~16 h until deemed complete as indicated by TLC (9:1 hexane:EtOAc). The reaction mixture was adjusted to pH~7 with saturated ammonium chloride. The solution was concentrated and purified by column chromatography (using 95:5 hexane:EtOAc as the eluent) to give 0.134 g (95% yield) of dronabinol (98.6% a/a HPLC purity).

We claim:

1. A process of separating an individual tetrahydrocannabinol isomer of interest from a mixture containing two or more such isomers, which comprises: treating the mixture with an isocyanate or isothiocyanate of formula I:

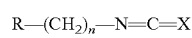

where R represents an aromatic ring optionally substituted with one or more electron withdrawing groups, with the proviso that R is not 3,5-dinitrophenyl n=0 or 1 and X is oxygen or sulphur; so as to produce a crytallizable THC compound of formula II:

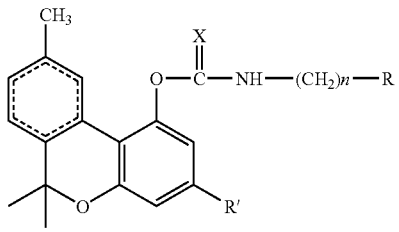

wherein X, n and R are as defined above, R' is a $C_3$-$C_{10}$ alkyl group and the dotted lines indicate optional unsaturation; forming a solution of the compound of formula II so formed in an organic solvent; separating the compound of formula II by crystallization from the solution in isolation of other THC derivatives; and hydrolyzing the compound of formula II to form the individual tetrahydrocannabinol isomer of interest.

2. The process of claim 1 wherein X represents oxygen.

3. The process of claim 1 wherein R represents aromatic group, optionally carrying one or more nuclear substituents independently selected from halo, cyano, sulfonate, carboxylate, carboxylic acid, aldehyde, keto, nitro, tertiary amino, trichloromethyl and trifluoromethyl.

4. The process of claim 3 wherein R represents an unsubstituted phenyl group.

5. The process of claim 4 wherein the tetrahydrocannabinol isomer of interest is dronabinol.

6. The process of claim 5 wherein the mixture containing dronabinol is treated with benzyl isocyanate to form a compound of formula IIa:

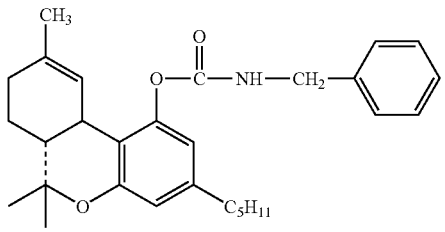

the compound of formula IIa is separated from the reaction, and then hydrolyzed to prepare dronabinol in isolation from other THC compounds.

7. Crystalline tetrahydrocannabinol carbamate derivatives of the general formula:

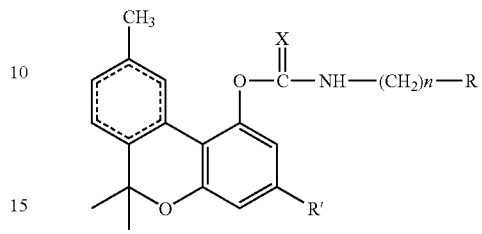

wherein R' is a $C_3$-$C_{10}$ alkyl group; n is 1; X is oxygen or sulphur; and R is an electron-withdrawing aromatic group, with proviso that the electron-withdrawing group is not 3,5-dinitrophenyl; and the dotted lines indicate optional unsaturations.

8. Tetrahydrocannabinol carbamate derivatives according to claim 7 wherein R represents a phenyl group or a naphthyl group, optionally carrying one or more nuclear substituents independently selected from halo, cyano, sulfonate, carboxylate, carboxylic acid, aldehyde, keto, nitro, tertiary amino, trichloromethyl and trifluoromethyl.

9. Tetrahydrocannabinol carbamate derivatives according to claim 7 wherein R represents a phenyl group.

10. Tetrahydrocannabinol carbamate derivatives according to claim 9 wherein X represents oxygen.

11. Tetrahydrocannabinol carbamate derivatives according to claim 10 wherein R' presents pentyl.

12. Crystalline dronabinol carbamate of the formula:

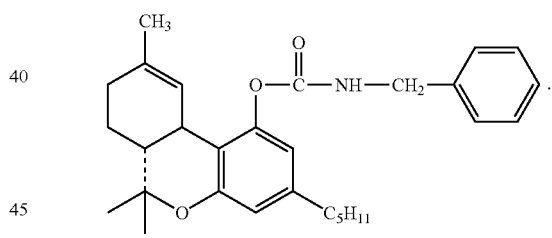

* * * * *